(12) United States Patent
Meuchel

(10) Patent No.: US 8,485,567 B1
(45) Date of Patent: Jul. 16, 2013

(54) STERILIZATION CASSETTE

(76) Inventor: Dennis A. Meuchel, Missoula, MT (US)

( * ) Notice: Subject to any disclaimer, the term of this patent is extended or adjusted under 35 U.S.C. 154(b) by 489 days.

(21) Appl. No.: 12/635,211

(22) Filed: Dec. 10, 2009

Related U.S. Application Data

(60) Provisional application No. 61/201,438, filed on Dec. 10, 2008.

(51) Int. Cl.
*E05C 1/02* (2006.01)

(52) U.S. Cl.
USPC 292/137; 292/80; 292/DIG. 61; 292/DIG. 63

(58) Field of Classification Search
USPC ........ 292/1, 80, 138, 145–147, 152, DIG. 11, 292/DIG. 63, DIG. 61, 137
See application file for complete search history.

(56) References Cited

U.S. PATENT DOCUMENTS

| | | | | |
|---|---|---|---|---|
| 1,632,832 A | * | 6/1927 | Gold | ............................ 292/152 |
| 1,653,015 A | * | 12/1927 | Koelln | ........................ 292/152 |
| 5,340,551 A | | 8/1994 | Berry, Jr. | |
| 5,451,379 A | | 9/1995 | Bowlin, Jr. | |
| 5,725,097 A | | 3/1998 | Bettenhausen et al. | |
| 6,113,867 A | | 9/2000 | Mayer | |
| 6,534,000 B1 | | 3/2003 | Michaelson et al. | |
| 6,554,327 B1 | * | 4/2003 | Riley | ............................ 292/152 |
| 6,592,000 B1 | * | 7/2003 | Owens et al. | ................. 220/324 |

* cited by examiner

*Primary Examiner* — Carlos Lugo
*Assistant Examiner* — Mark Williams
(74) *Attorney, Agent, or Firm* — Jean Kyle

(57) ABSTRACT

A sterilization cassette has a slide latch system to secure the lid of the cassette to the body of the cassette. A finger tab on the outside of the cassette moves a latch arm on the inside of the cassette along a slot. A tension spring secures the position of latch components whether the latch is open or closed. Spacers between the cassette and latch parts facilitate smooth gliding action. The latch arm engages an angled bracket on the lid of the cassette. Alternating notch depths on instrument rails within the cassette work with opposing rails that likewise have alternating depths of notches to capture and hold instruments. This notch configuration causes the handles of adjacent instruments stowed in the cassette to stagger in height so that a clinician can access the handles of the stowed instruments.

7 Claims, 8 Drawing Sheets

STERILIZATION CASSETTE

CROSS-REFERENCE TO RELATED APPLICATIONS

This application claims the benefits of U.S. Provisional Application No. 61/201,438, filed Dec. 10, 2008, the disclosure of which is hereby incorporated by reference in its entirety including all figures, tables and drawings.

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISC APPENDIX

Not applicable

FIELD OF THE INVENTION

This invention relates to a cassette and tray system wherein cassettes of varying sizes and internal configurations are used to securely hold collections of dental/medical instruments. Such cassettes maintain a secure and orderly arrangement of desired instrumentation during the office procedure and/or particularly in the cleaning operation during the sterilization process.

BACKGROUND OF THE INVENTION

Sterilization cassettes are typically a square or rectangle box with a bottom, or body and a mating lid; the lid is often held to the bottom with a hinge. Traditionally most cassettes are made of stainless steel sheet material which has been perforated to allow sterilizing steam to enter the cassette. A cassette blank is bent to form a shallow sided box with the backside of the box often including hinge cleats. Box depth is typically ¾ inch to 2 inches. The lid is similarly constructed. The lid can also have a series of hinge cleats along one side. Sterilization cassettes can also be made of resin. The lid and box are fastened to one another to trap instruments to be sterilized inside. Traditionally, the lid is connected to the box on one side by a hinge and fastened on the other with a clip or latch. Alternatively, the lid can be secured to the box with an arrangement of slots and mating tabs. This allows the lid to be removed from the box after sterilization. Deficiencies in the latching or fastening mechanism used to secure the lid to the bottom compartment cause a great deal of consternation in many available cassette designs.

The interior of a cassette can contain a series of standoff rails to hold long instruments and divided compartments to hold small or inconsistently shaped instruments. Rivets and/or spot welding secure the internal dividers and rails, or if the cassette is made of resin these dividers are injection molded. Traditionally, instrument rails have some sort of scalloped design or extended fork slots in which to align and hold the instruments side by side in the bottom of the cassette. Most commonly these bottom rails are made of stainless steel or are a silicone strips attached to the bottom of the main compartment. Instruments are dropped into scalloped cradles in the rail or pressed between flexible silicone fingers on the silicone strip to securely retain the instruments in the cassette. If stainless steel instrument scalloped rails are used, a strip of silicone tubing is attached across the lid, thereby providing a means to retain the instruments within the scalloped cradles when the lid is closed protecting the instruments from damage during the sterilization procedure. The scallops or fingers of a rail are arranged to accommodate a maximum number of instruments. This causes difficulty however when there is not enough space between neighboring instruments to allow the clinician to remove the chosen instrument in a safe manner. The clinician is forced to grab the instrument by its sharp working end where there is adequate finger room to remove it from the cassette. Sterility can be compromised if the sharp end cuts through the glove on a hand.

Current cassette lids use silicone exclusively as a means of retention to hold instrument in place. It is becoming increasingly undesirable to use silicone in or on products that require sterilization. It has been recognized that silicone traps debris beneath its layer and shields or insulates that debris from the effects of sterilization.

A need remains for a sterilization cassette with a reliable, easy to use latching system with an internal configuration that holds instruments conveniently for the clinician yet holds them securely and without the use of silicone.

All patents, patent applications, provisional patent applications and publications referred to or cited herein, are incorporated by reference in their entirety to the extent they are not inconsistent with the teachings of the specification.

BRIEF SUMMARY OF THE INVENTION

A sterilization cassette is described that has a bottom compartment that houses instruments in a compact side-by-side arrangement, yet allows the clinician to remove sharp instruments by their handles and not by their sharp working tips. The height of instruments is staggered within a scalloped rail where one end of an instrument is up and the same end of the adjacent instruments are down. This arrangement creates a crisscross pattern in the instrument racks allowing the clinician to grab an instrument handle instead of grabbing the dental instrument by its tip. Additionally, the present invention does not use silicone as a retention means to hold instruments in place within the closed cassette. A contoured stainless steel retention rails and/or flat protruding spring fingers affixed to the lid is used to secure and hold individual instruments in place in the cassette of the subject invention. The use of a non-insulating material for retention, such as metal, allows for a more effective sterilization action.

A unique slide latch design made of stainless steel mated with polytetrafluoroethylene slides allows the latch arm to smoothly engage a stainless bracket on the lid of the cassette. The components of the slide latch are assembled about an elongated slot in the front bottom of the box. A finger tab or thumb knob positioned on the front of the box is secured to a metal latch arm inside the box. Sandwiched between the finger tab and the latch arm is a spring tempered tension washer. A piece of polytetrafluoroethylene slide is positioned between the finger tab and the front of the box. A second polytetrafluoroethylene slide is positioned between the latch arm and the inner box front wall. An angle bracket is affixed onto the lid to engage the latch arm and complete the latching system.

DETAILED DESCRIPTION OF THE INVENTION

Figure 1:
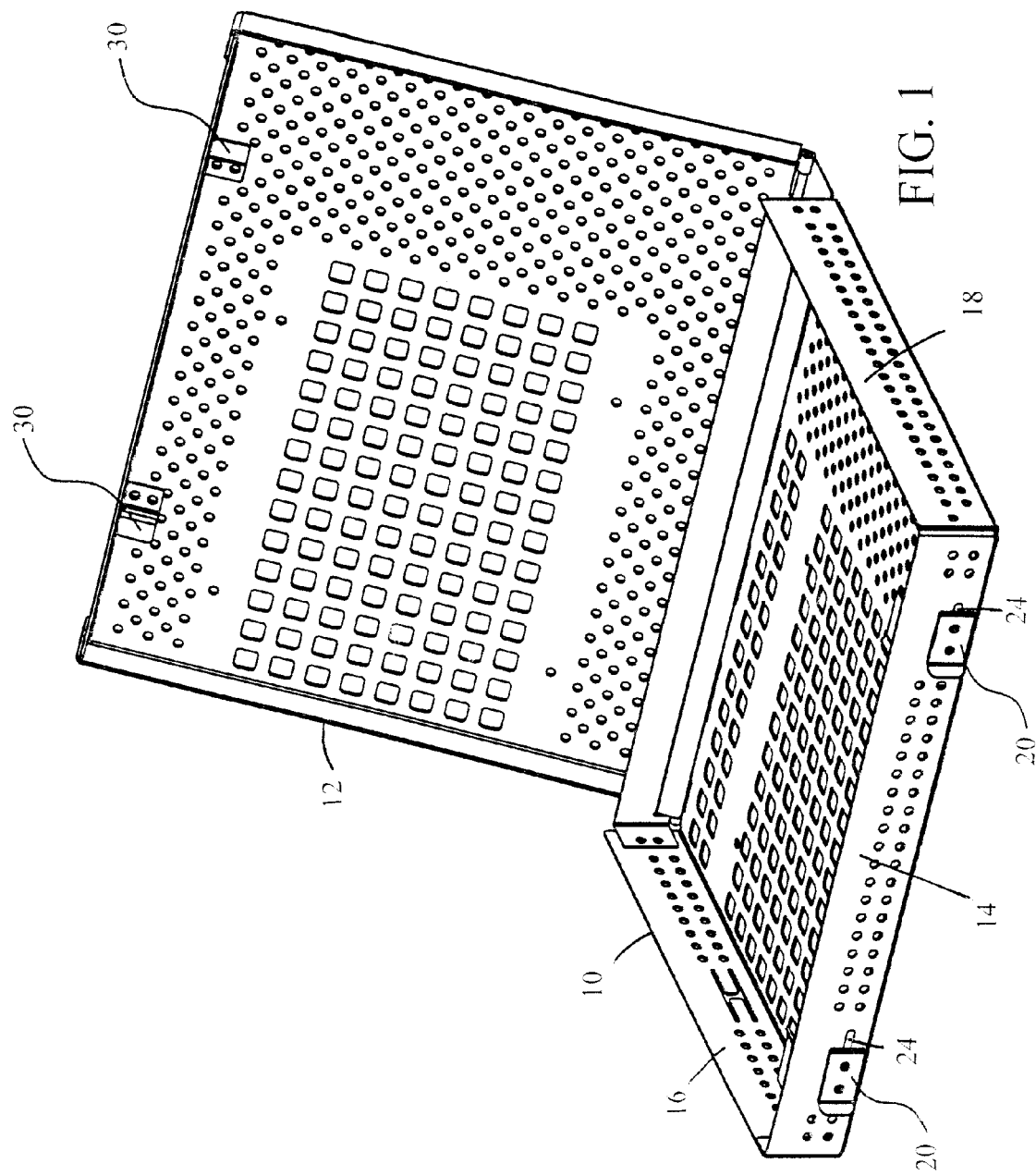
FIG. 1 is a perspective view of a preferred embodiment of a sterilization cassette of the subject invention showing the front finger slide tabs and securing right angle bracket affixed to the lid.
Figure 2:
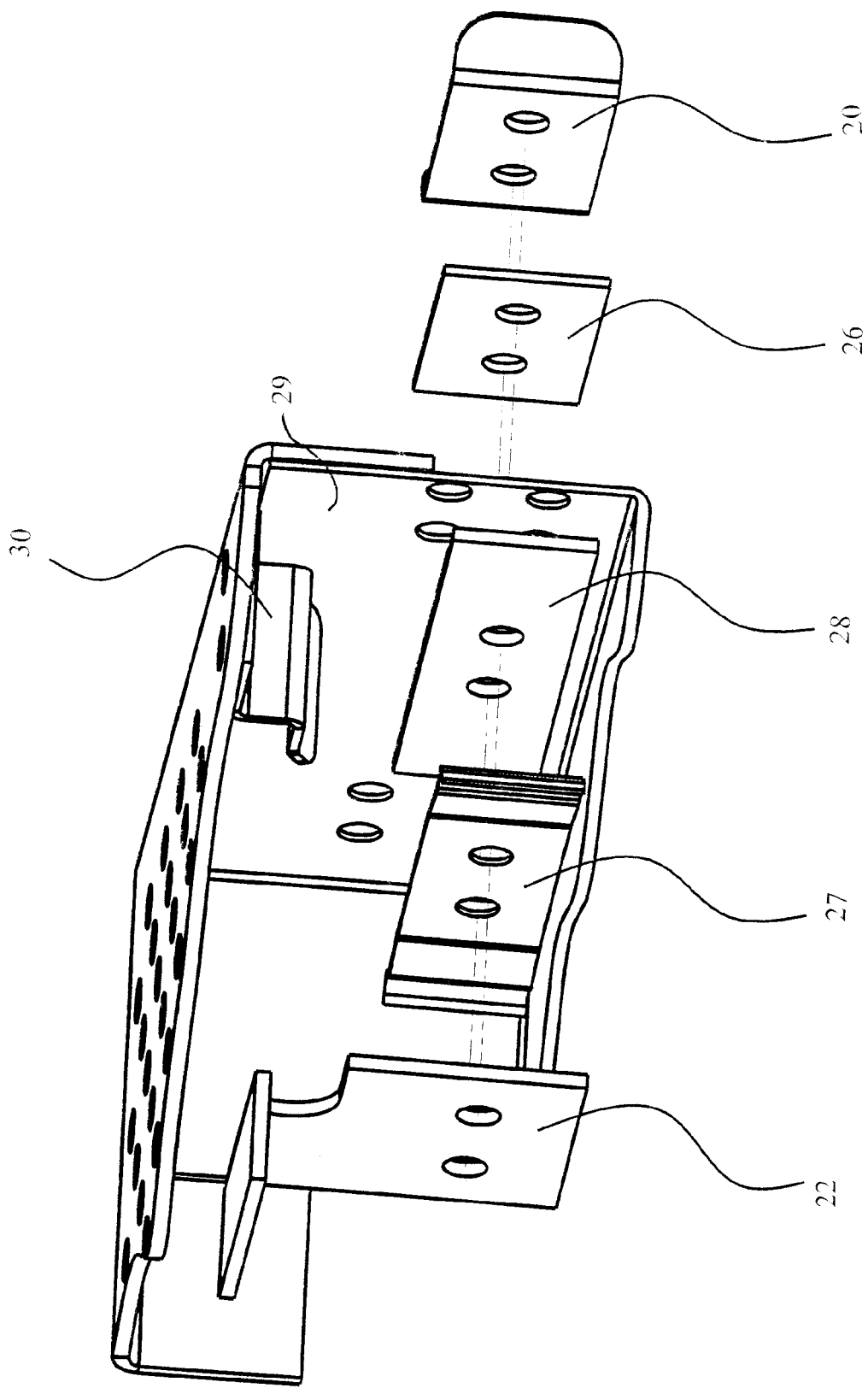
FIG. 2 is an exploded view of a latch element on a preferred embodiment of a sterilization cassette of the subject invention.
Figure 3:
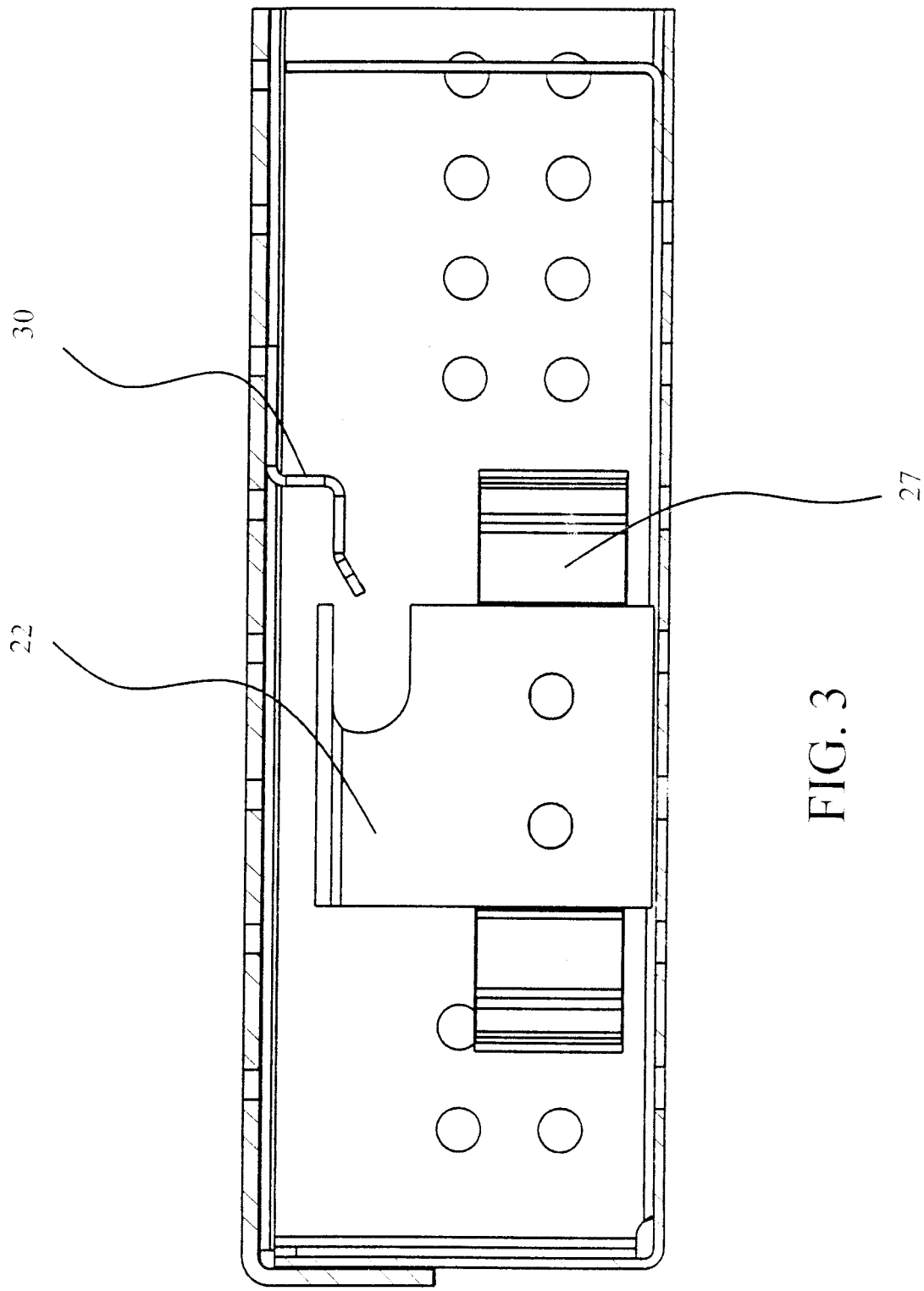
FIG. 3 is a cross-sectional rear view of a preferred embodiment of a sterilization cassette showing the interior of the box and the latch in the open position.
Figure 4:
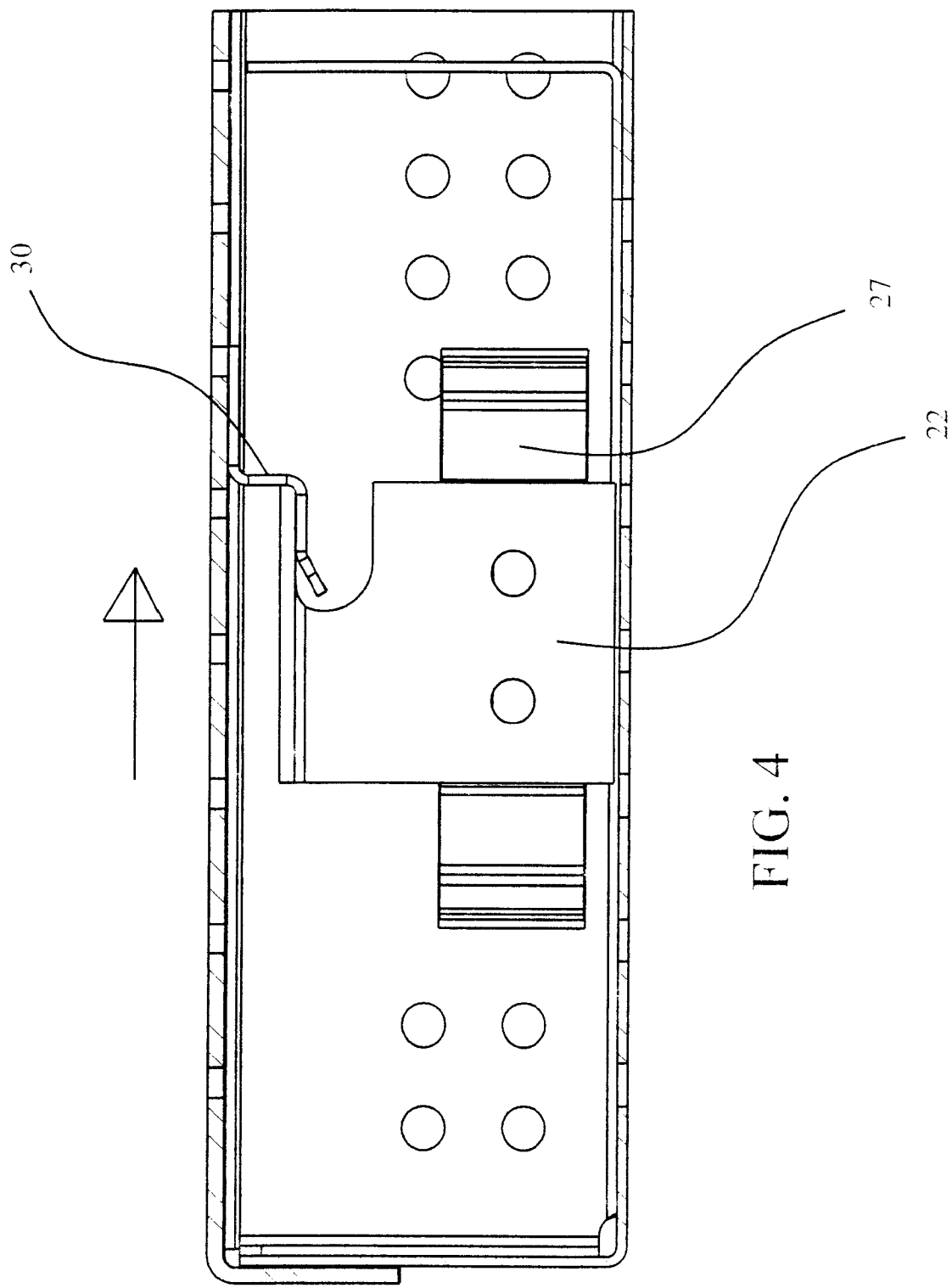
FIG. 4 is a cross-sectional rear view of a preferred embodiment of a sterilization cassette showing the interior of the box and the latch in the closed position.
Figure 5:
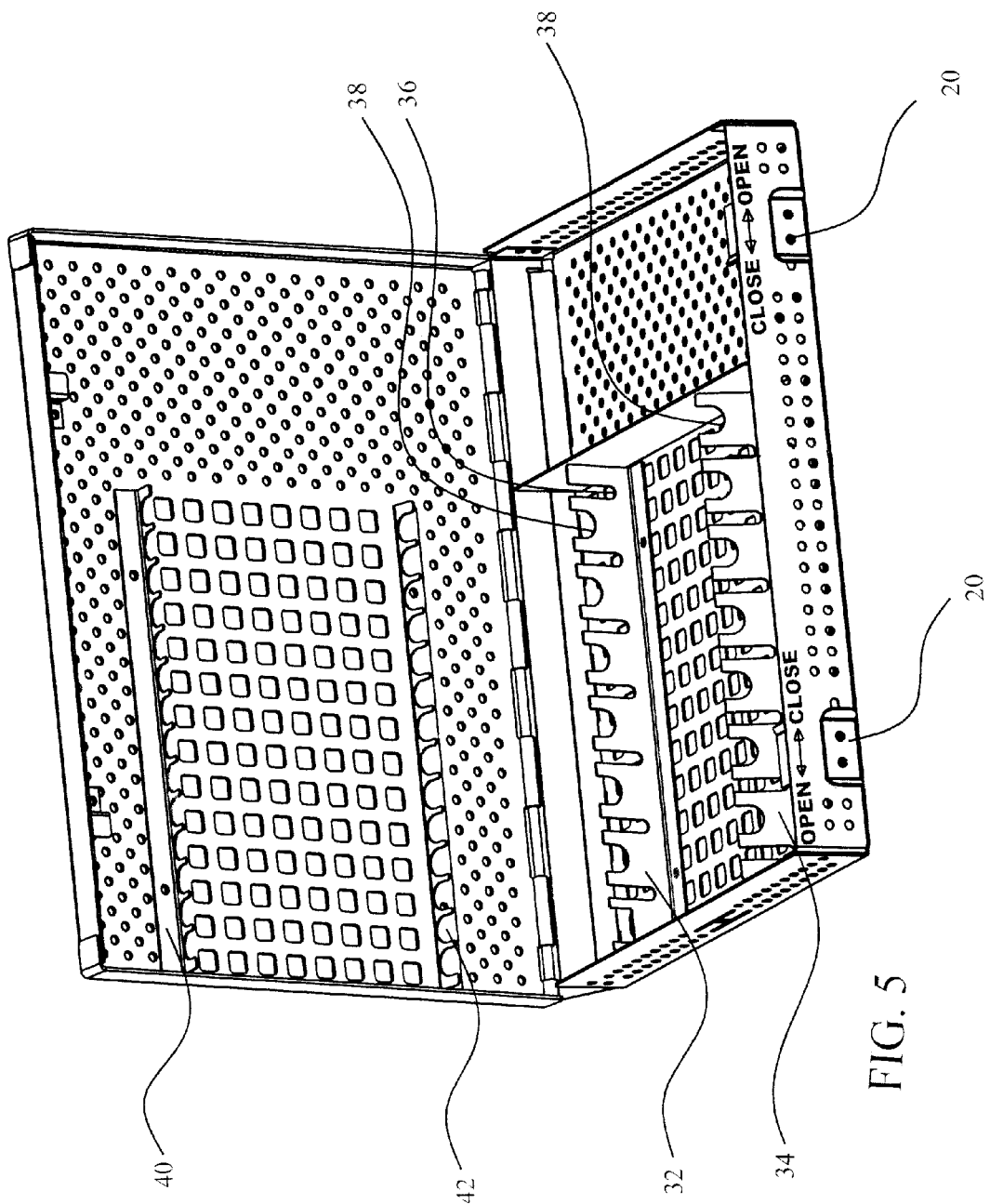
FIG. 5 is a perspective view of a preferred embodiment of the sterilization cassette of the subject invention showing a preferred rail configuration.
Figure 6:
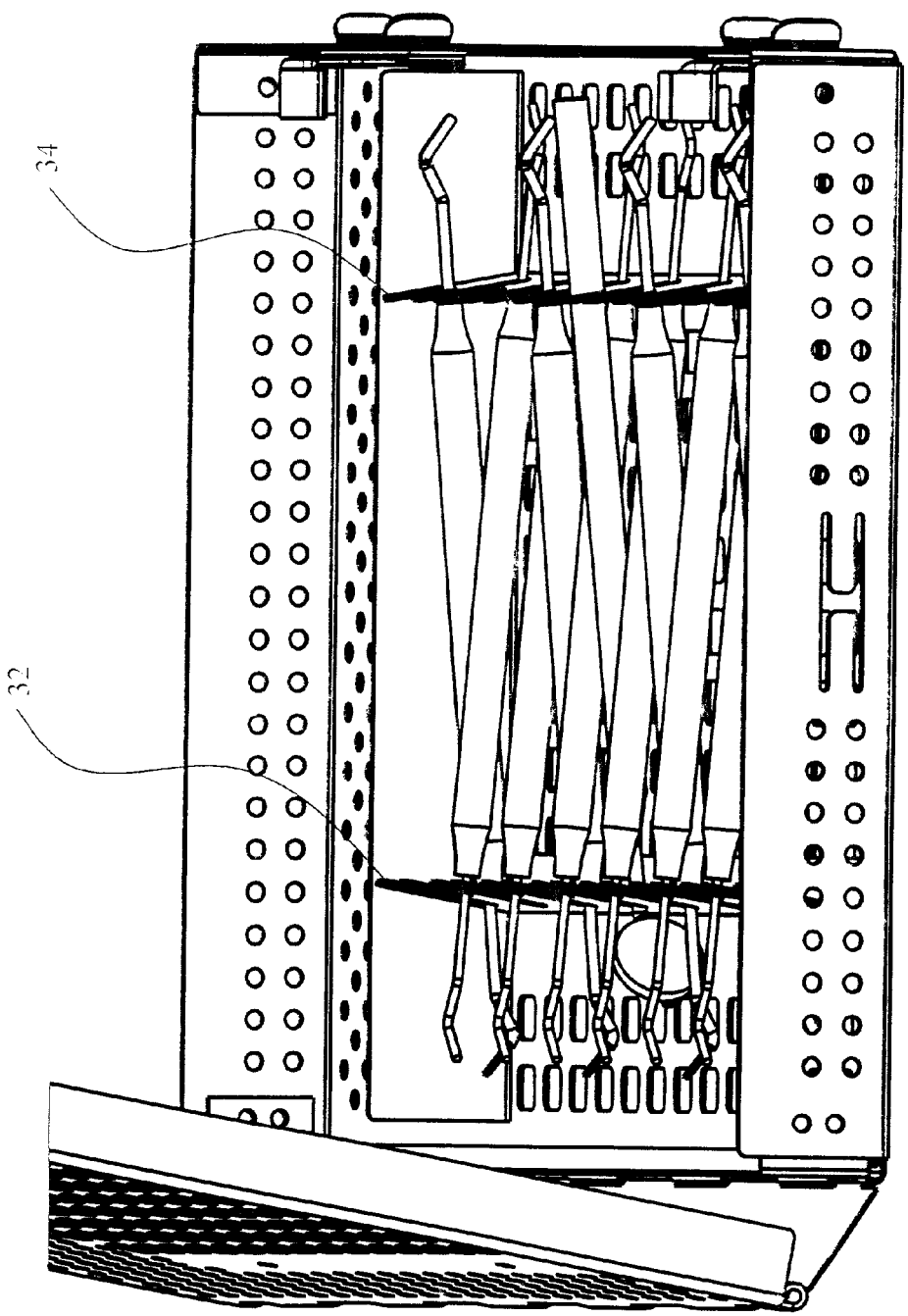
FIG. 6 is a side perspective view of instruments in a preferred embodiment of the sterilization cassette of the subject invention showing the staggered positioning of the instruments in the rails.

The invention involves an improved sterilization cassette with an easily engagable latch to lock instruments to be sterilized within the cassette. A unique rack system securely holds the instruments in the cassette without using silicone, yet presents the handles of the instruments to the clinician for easy removal from the cassette.

The latch assembly for use on the cassettes of the subject invention is a slide latch that is easy to use yet securely keeps the lid closed under the most extreme handling conditions. A preferred embodiment of the subject latch system is shown in FIGS. 1-4. Stainless steel is the preferred material for the slide latch, however any metallic material, such as titanium, or aluminum with a protective hard coating, or resin/plastic, and nylon can be used. Materials for the latch are preferably all non-insulating materials. The locking slide latch or simple slide latch slides to engage an accommodating bracket secured to the lid 12 of the cassette. A thumb grip or finger tab is positioned on the outer front 14 of the main body 10 of the cassette. One skilled in the art would recognize that the sliding latch system of the subject invention could be located on the sides 16, 18 of the cassette body as well, and still function effectively. The finger tab 20 is attached to an internal latch arm 22 through a slotted hole 24 by, for example, riveting, spot welding, screws, welding, or brazing. A spacer 26 is disposed between the finger tab 20 and the outside wall of the front 14 of the body of the cassette and an opposing spacer 28 is positioned between the latch arm 22 and the inside wall 29 of the front of the cassette to provide a smooth sliding action. The spacers can be any material that facilitates slide yet is resistant to the sterilization process. In a preferred embodiment, the spacers are rectangular pieces of polytetrafluoroethylene. A tension spring 27 is positioned between spacer 28 and latch arm 22 to maintain latch arm position whether the latch is open or closed. The latch arm 22 engages an angle bracket 30 attached to the lid 12 of the cassette. One skilled in the art recognizes that latch components can be reversed so that the slide is on the lid and the bracket is on the body. The subject sliding latch successfully secures the lid 12 and the body 10 of the cassette together. The sliding spacers and positive spring tension of the latch prevent the latch from failing during sterilization and make the latch easy to manipulate.

The sterilization cassette of the subject invention further comprises a unique rack system to hold long handled instruments that eliminates the use of silicone and to present the sterilized instruments to a clinician so they will not find it necessary to grab an instrument by its tip. Preferred embodiments of the subject rack system are shown in FIGS. 5-8. The rack system comprises a pair of opposing rails 32, 34. Each rail has a series of slots to receive a portion of an instrument. The slots alternate in depth between deep slots 36 and shallow slots 38. Slots can be v-notches and/or rounded scallops. Spring fingers made from sheet stock can be used to secure irregular shaped tools. The series of alternating depth slots on one rail 32 also alternate with a series of alternating depth slots on the opposing rail 34. Therefore, a deep slot 36 on rail 32 opposes a shallow slot 38 on rail 34. This allows instruments to be placed side-by-side so that every other instrument handle is angled toward the bottom of the box, while its immediate neighboring instrument handle is angled upward (see FIG. 6).

In the exemplified embodiment, a shallow, large radius scallop is shown next to a deep, narrow radius scallop. If these scallops were all large radius scallops the narrow peaks between the scallops on the top of the rack would be pointy and sharp. Additionally, the narrow peaks would be weak and likely to bend. If the scallops were all narrow scalps then a single-end dental instrument of typical handle size ¼ inches in diameter or larger, usually ⅜ inches round would not sit in the scallop deep enough to allow the lid to close. Thus, it is preferred that scallop width is varied along the rail. This combination allows the handle end of every other instrument to be held up thus giving enough spacing between the instrument handles to grab a single instrument with fingers. Typically, when dental instrument handles are all in the same plane there is not enough room to remove the instrument by the handle. The only other option is to grab the instrument by the sharp tip, which although considered acceptable practice, can be dangerous. The crisscross rack system of the subject invention allows instruments to be close to each other which is critical in keeping the overall cassette length to a minimum. By just spacing the dental handles far enough apart to allow for a safer means of removing the instrument by the handle the cassette footprint would be much to long to fit into most sterilization units.

Figure 7:
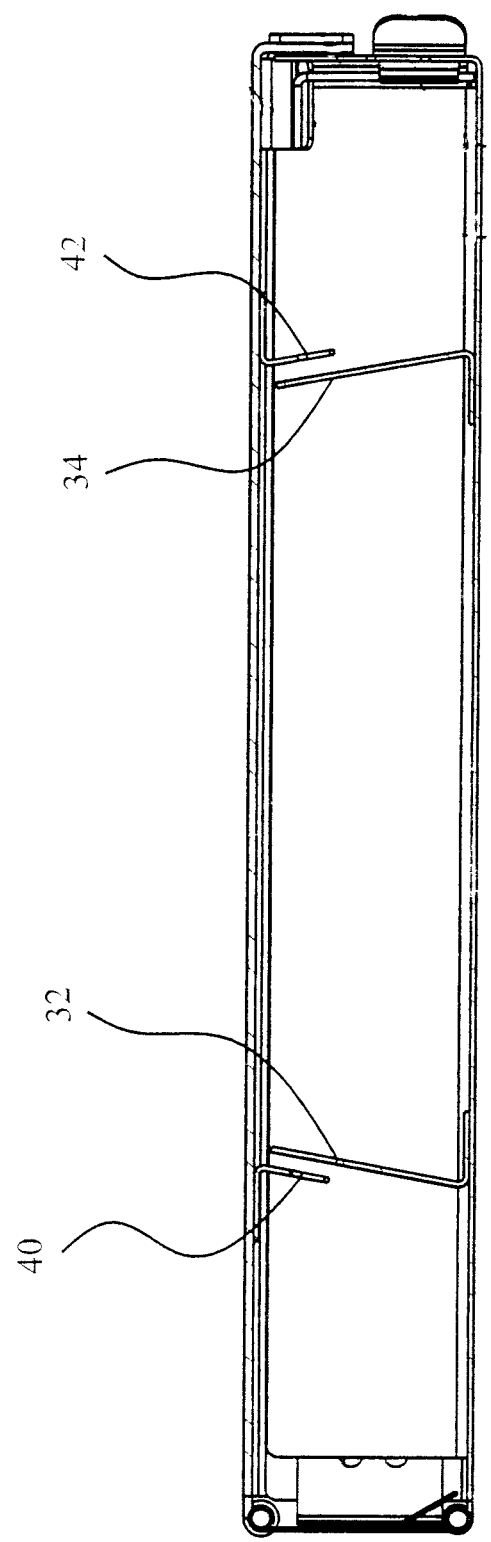
FIG. 7 is a cross-sectional side elevational view of a preferred embodiment of the sterilization cassette of the subject invention the closed cassette showing angled rails on the bottom of the cassette matching angled retention rails on the lid of the cassette.
Figure 8:
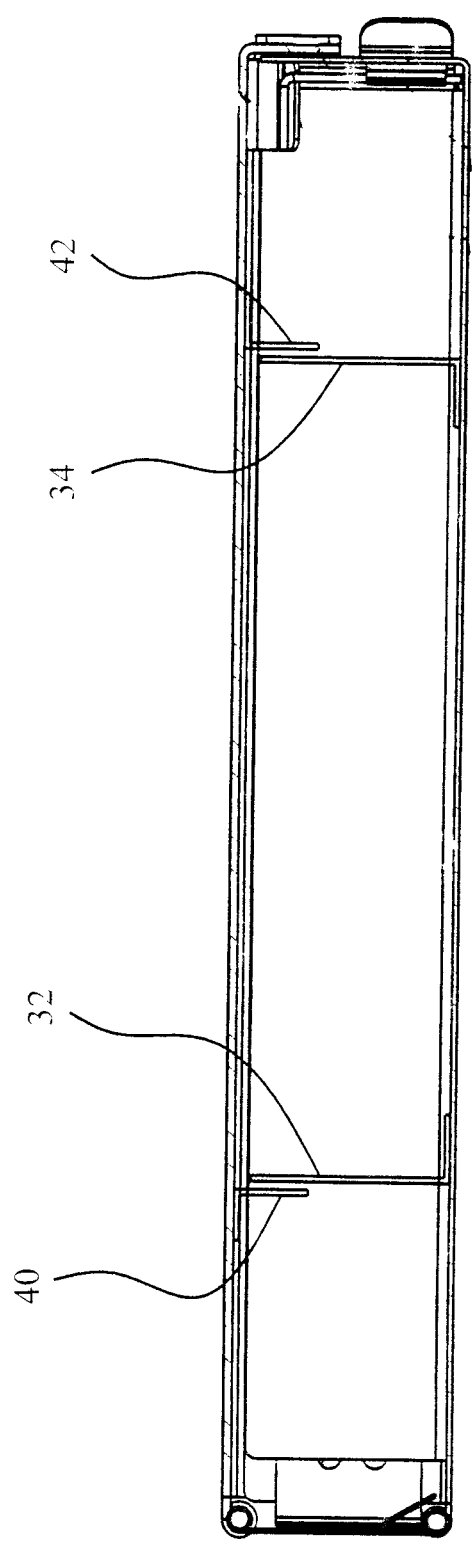
FIG. 8 a cross-sectional side elevational view of another preferred embodiment of the sterilization cassette of the subject invention the closed cassette showing straight rails on the bottom of the cassette matching straight retention rails on the lid of the cassette.

In a particularly preferred embodiment, rails are angled inward toward one another. The angle of the rails forces the long cylindrical dental instruments downward, which aids in keeping the instruments from jiggling top to the bottom in the closed cassette. Instruments resting in an angled rail are further secured within the cassette as the lower end of the instrument is wedged beneath the opposing angled rail. The exemplified embodiment shows the rails angled at from about 10 degrees to about 20 degrees and preferably about 15 degrees (FIG. 7).

Top rails 40, 42 hold the bottom instruments in place when the lid on the cassette is closed. A contoured retention rail is shown in the exemplified embodiment. Suitable retention rails can included however flat protruding spring fingers, a simple bar, or an angle bar. While the exemplified embodiment shows a top and lower rail to secure and hold instruments in place it is noted that if the height of the bottom instrument rack is the same as the depth of the body 10 of the cassette the lid 12 can serve as the retaining mechanism to hold the instruments in place in the rails in the closed cassette.

The rack system of the subject invention should be made of non-insulating materials. It is important that non-insulating materials contact the instruments during the sterilization process. While stainless steel is preferred, titanium, anodized aluminum, plastic or, wire rod, or wire bar can be used to achieve the desired construction. The subject rails can be secured to the cassette by a variety of means, including, but not limited to, riveting, screwing, and spot welding. The sterilization cassette of the subject invention can be made customizable by securing specifically configured rails to the cassette as snap in clips, or with retaining tabs on the rail.

It is understood that the foregoing examples are merely illustrative of the present invention. Certain modifications of the articles and/or methods may be made and still achieve the objectives of the invention. Such modifications are contemplated as within the scope of the claimed invention.

The invention claimed is:

1. A sterilization cassette having mating pieces to form a closed compartment, the sterilization cassette including a latch comprising;
   a finger tab on an outside surface of a first piece of the cassette;
   a first spacer connected to the finger tab and disposed between the finger tab and the outside surface of the first piece of the cassette, wherein the first spacer facilitates sliding of the finger tab and the first spacer along the outside surface of the first piece of the cassette;
   a latch arm on an inside surface of the first piece of the cassette, the latch arm connected to the finger tab through an elongated slot in the first piece;
   a second spacer disposed between the latch arm and the inside surface of the first piece of the cassette, wherein the second spacer facilitates sliding of the latch arm and the second spacer along the inside surface of first piece of the cassette;
   a tension spring disposed between the latch arm and the second spacer, the tension spring holding the finger tab and the first spacer against the outside surface of the first piece and the latch arm and the second spacer against the inside surface of the first piece preventing the finger tab and the first spacer and the latch arm and the second spacer from sliding freely along the elongated slot; and
   a bracket connected to a second piece of the cassette, wherein the bracket on the second piece of the cassette is captured by the latch arm and held by the tension spring on the first piece of the cassette and the latch is in the closed position when the pieces are mated forming a closed compartment.

2. The sterilization cassette of claim 1, wherein said bracket is an angle bracket.

3. The sterilization cassette of claim 1, wherein said first piece and said second piece are connected by at least one hinge.

4. The sterilization cassette of claim 1, wherein said first piece is a body of said cassette and said second piece is a lid of said cassette.

5. The sterilization cassette of claim 3, wherein at least one latch is opposite said at least one hinge.

6. The sterilization cassette of claim 3, wherein at least one latch is adjacent said at least one hinge.

7. The sterilization cassette of claim 1, wherein at least one of said first spacer and said second spacer is polytetrafluoroethylene.

* * * * *